United States Patent [19]
Tada et al.

[11] 4,368,339

[45] Jan. 11, 1983

[54] PROCESS FOR THE ISOMERIZATION OF A HALOGENATED TOLUENE

[75] Inventors: Kuniyuki Tada, Kamakura; Eiichi Minomiya, Odawara; Takehisa Inoue, Tokyo, all of Japan

[73] Assignee: Toray Industries, Incorporated, Japan

[21] Appl. No.: 290,238

[22] Filed: Aug. 5, 1981

[30] Foreign Application Priority Data

Aug. 25, 1980 [JP] Japan ................................ 55-115898

[51] Int. Cl.³ ............................................. C07C 17/24
[52] U.S. Cl. .................................................... 570/202
[58] Field of Search ......................................... 570/202

[56] References Cited

U.S. PATENT DOCUMENTS 3,560,579 2/1971 Bacha et al. ...................... 570/202

*Primary Examiner*—Charles F. Warren
*Assistant Examiner*—Joseph A. Boska
*Attorney, Agent, or Firm*—Scully, Scott, Murphy & Presser

[57] ABSTRACT

Provided is a process for isomerizing a halogenated toluene using an acid form of zeolite as a catalyst.

8 Claims, No Drawings

PROCESS FOR THE ISOMERIZATION OF A HALOGENATED TOLUENE

BACKGROUND OF THE INVENTION

This invention relates to a process for the isomerization of a halogenated toluene.

The halogenated toluene as referred to herein is a compound resulting from substitution of one hydrogen atom attached to the toluene nucleus by a halogen atom, and it is o-, m- or p-halotoluene.

In general, a halogenated toluene is obtained by a nuclear substitution reaction of toluene with halogen. This halogenation reaction is a strongly o,p-orienting reaction, so that in case it is desired to obtain m-isomer, it is necessary to isomerize o- or p-isomer. The ratio of demand for the halotoluene isomers is in many cases different from their production ratio at the time of halogenation. Therefore, in order to utilize halogenated toluenes effectively, the isomerization process has an important technical meaning.

As conventional examples of such an isomerization reaction there have been known the method disclosed in Olah, G. A., "J. Org. Che." 27, 3464 (1962) which uses aluminum chloride etc. as a catalyst and the method disclosed in Japanese Patent Publication No. 11809/71 which uses $HF$-$BF_3$ as a catalyst. However, these conventional methods for the isomerization reaction involve problems such that the catalyst activity is not sufficient and a long reaction time or a large amount of catalyst is needed, and further that the reaction vessel is corroded and it is difficult to separate the reaction product from catalyst components. Thus, none of them have been desirable as industrial isomerization methods.

SUMMARY OF THE INVENTION

It is an object of this invention to overcome the foregoing disadvantages associated with the prior art.

It is another object of this invention to provide a process for efficient isomerization of a halogenated toluene at a high catalyst activity while suppressing the formation of by-products.

Other objects and advantages of this invention will become apparent from the following description.

The aforesaid objects of this invention can be attained by a process for the isomerization of a halogenated toluene characterized by contacting the halogenated toluene with an acid form of zeolite.

DETAILED DESCRIPTION OF THE INVENTION

Halogenated toluenes to be fed in the isomerization reaction of this invention are o-, m- and p-halotoluenes. The halogen in these halogenated toluenes may be chlorine, bromine, iodine and fluorine, but chlorine is most general.

Zeolites which may be used in the invention involve both natural and synthetic zeolites provided they must have a pore diameter permitting a halogenated toluene to diffuse thereinto under reaction conditions. And there is no special limit to their crystal structure. However, since the zeolite used in the isomerization reaction of the invention functions as a solid acid catalyst, a too low atomic ratio of silicon to aluminum is not desirable because it would cause lowering in acid strength and insufficiency of catalyst activity. Zeolites which are used preferably have a silicon to aluminum atomic ratio of not less than 2, and particularly preferred is mordenite.

In the isomerization reaction of the invention there are used acid form of zeolites. Acid form of zeolites, as well known, contain $H^+$, $NH_4^+$, or di- or higher polyvalent cations such as rare earth ions, which are obtainable usually by ion-exchanging at least a part of alkali metal ions of zeolite such as sodium with proton, ammonium cation or a polyvalent cation.

The cation exchange amount greatly affects the solid acidity of zeolite, and it is preferable that the atomic ratio of monovalent alkali metal to aluminum atom in the zeolite be as small as possible and particularly preferably not more than 0.1. The ion exchange of zeolite with the foregoing cations may be carried out by known ion-exchange techniques. For example, the ion exchange can be performed easily by treating zeolite with an aqueous solution containing an acid such as hydrochloric acid, an ammonium salt such as ammonium nitrate or a water-soluble salt of a polyvalent cation.

The zeolite used in the isomerization process of this invention usually is in the agglomerated bodies such as granules. There is no special limit to the agglomeration method for the zeolite. Known methods such as rolling, extrusion and compression molding methods are applicable. Binders such as alumina sol and clay may be added in the agglomeration of zeolite. The foregoing ion-exchange treatment may be applied either before or after such agglomeration operation.

The acid form of zeolite bodies thus prepared is activated by calcination usually at 300°–600° C. and then used as catalyst in the isomerization process of this invention. The isomerization process of this invention resides in a catalytic isomerization of a halogenated toluene using the catalyst thus prepared.

Such a reaction can be performed according to various known isomerization procedures, but from the ease of operation the fixed-bed flow type reaction is particularly preferred. The reaction temperature usually ranges from about 200° to about 500° C., particularly preferably from about 200° to about 400° C. The isomerization reaction of this invention may be carried out in the presence of hydrogen, an aromatic hydrocarbon or a halogenated aromatic with a view to prolonging the catalyst life or reducing side reactions. Particularly, if the isomerization reaction is conducted in the presence of a halogenated benzene corresponding to the halogenated toluene, there are obtained preferable results.

Working examples of this invention will be described hereinunder to further illustrate the invention.

EXAMPLE 1

A sodium type synthetic mordenite was dealkalized at about 90° C. using a 10% by weight aqueous ammonium nitrate solution to obtain an acid form of the synthetic mordenite. The Si/Al and Na/Al ratios of the zeolite thus obtained were 5.6 and 0.03, respectively. This dealkalized zeolite was mixed with alumina sol in an amount of 10% by weight in terms of $Al_2O_3$, and then the mixture was kneaded. The mixture was extruded into glanules of 20 to 24 mesh, which was calcined in air at 500° C. for 2 hours to prepare a catalyst.

20 g. of the so-prepared catalyst was charged into a reaction tube and there was performed an isomerization reaction of orthochlorotoluene (o-CT) under the following reaction conditions.

Feed composition: o-CT/CB=1/2 wt/wt
$N_2$/feed: 5/1 mol/mol

Feed amount: 8 g/hr
Reaction temperature: 320° C.
Reaction pressure: 20 kg/cm$^2$ The composition of CT after reaction was o-CT 68.0%, m-CT 25.1% and p-CT 6.9%, and as side reaction products there were produced 0.2 wt.% of B+T and 0.1 wt.% of DCB+CX, in which the abbreviations have the following meaning.
CB: chlorobenzene
B: benzene
T: toluene
DCB: dichlorobenzene
CX: chloroxylene
m-CT: metachlorotoluene
p-CT: parachlorotoluene

EXAMPLE 2

Using the catalyst obtained in Example 1 there was performed an isomerization reaction of o-CT in liquid phase under the following reaction conditions.
Feed composition: o-CT/CB=1/1 wt/wt
Feed amount: 22.9 g/hr
Catalyst amount: 25 g.
Reaction temperature: 300° C.
Reaction pressure: 25 kg/cm$^2$ The composition of CT after reaction was o-CT 65.2%, m-CT 27.6% and p-CT 7.2%, and as side reaction products there were formed 0.4 wt.% of B+T and 0.3 wt.% of DCB+CX.

EXAMPLE 3

Using the catalyst obtained in Example 1 there was performed an isomerization reaction of p-CT in liquid phase under the following reaction conditions.
Feed composition: p-CT
Feed amount: 10.7 g/hr
Catalyst amount: 25 g.
Reaction temperature 275° C.
Reaction pressure: 25 kg/cm$^2$ The composition of CT after reaction was o-CT 0.7%, m-CT 15.6% and p-CT 83.7%, and as side reaction products there were obtained 1.1 wt.% of B+T+CB and 0.6 wt.% of DCB+CX.

Comparative Example 1

Using a silica-alumina catalyst ("N-632-L," a product of Nikki Chemical Co.) there was performed the same reaction as in Example 1. The silica-alumina catalyst exhibited little activity to the isomerization reaction of CT. The followings are the results of reaction carried out at a temperature higher by 30° C. than that in Example 1, i.e. 350° C.
Production of m-CT+p-CT: 0.3 wt.%
Production of B+T: 0.2 wt.%
Production of DCB+CX: little

EXAMPLE 4

Y type zeolite powder ("SK-40," a product of Union Carbide Corp.) was mixed with alumina sol in an amount of 10% by weight in terms of Al$_2$O$_3$, and the mixture was kneaded, extruded and calcined in air at 500° C. for 1 hour to obtain a Y type zeolite granule of 20 to 24 mesh. This Y type zeolite granule was ion-exchanged three times (at a liquid/solid ratio of 1.8 l/kg and at about 90° C.) using a 10% by weight aqueous ammonium nitrate solution, then calcined in air at 500° C. for 1 hour, and further this ion-exchange and calcination operation was repeated twice to obtain a dealkalized, namely an acid form, of a Y type zeolite catalyst. The Si/Al and Na/Al ratios of the zeolite thus treated were 2.4 and 0.01, respectively.

Using 20 g. of this catalyst there was performed an isomerization reaction of o-CT under the same conditions as in Example 1. The composition of CT after reaction was o-CT 91.23%, m-CT 7.51% and p-CT 1.26%, and as side reaction products there were produced 1.4 wt.% of B+T and 0.4 wt.% of DCB+CX.

What is claimed is:

1. A process for the isomerization of a halogenated toluene characterized by contacting the halogenated toluene with an acid form of zeolite.

2. The process as defined in claim 1, in which said acid form of zeolite has an atomic ratio of silicon to aluminum of not less than 2.

3. The process as defined in claim 1, in which said acid form of zeolite has an atomic ratio of alkali metal to aluminum of not more than 0.1.

4. The process as defined in claim 1, in which said acid form of zeolite contains proton, ammonium ion, or rare earth ion as cation.

5. The process as defined in claim 1, in which said acid form of zeolite is an acid form of mordenite.

6. The process as defined in claim 1, in which said halogenated toluene is o-, m-, or p-halotoluene.

7. The process as defined in claim 6, in which said halogen is chlorine.

8. The process as defined in claim 1, in which said isomerization reaction is carried out at a temperature in the range of from about 200° C. to about 500° C.

* * * * *